US008443805B2

(12) United States Patent
Amarasinghe et al.

(10) Patent No.: US 8,443,805 B2
(45) Date of Patent: *May 21, 2013

(54) HEADGEAR ASSEMBLY FOR A RESPIRATORY MASK ASSEMBLY

(75) Inventors: Amal S. Amarasinghe, West Pennant Hills (AU); Perry D. Lithgow, Moruya (AU); Memduh Guney, Killara (AU)

(73) Assignee: ResMed Limited, Bella Vista (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/200,947

(22) Filed: Oct. 5, 2011

(65) Prior Publication Data

US 2012/0024290 A1 Feb. 2, 2012

Related U.S. Application Data

(63) Continuation of application No. 12/285,445, filed on Oct. 6, 2008, now Pat. No. 8,042,543, which is a continuation of application No. 10/655,602, filed on Sep. 5, 2003, now Pat. No. 7,509,958.

(60) Provisional application No. 60/424,694, filed on Nov. 8, 2002.

(51) Int. Cl.
| A62B 17/04 | (2006.01) |
| A62B 18/08 | (2006.01) |
| A62B 18/02 | (2006.01) |
| A62B 7/10 | (2006.01) |
| A61M 16/00 | (2006.01) |
| A42B 1/22 | (2006.01) |
| A61F 9/02 | (2006.01) |

(52) U.S. Cl.
USPC ............ 128/207.11; 128/201.22; 128/201.23; 128/201.19; 128/205.25; 128/205.29; 128/206.24; 128/206.26; 128/206.27; 128/206.28; 128/207.13; 128/207.17; 2/417; 2/418; 2/419; 2/420; 2/452

(58) Field of Classification Search
USPC ............ 128/201.22, 201.23, 201.19, 205.25, 128/205.29, 206.24, 206.26, 206.27, 206.28, 128/207.11, 207.13, 207.17; 2/9, 173, 417–420, 2/452; 24/71.1, 68 SK, 68 E, 194, 196, 484, 24/591.1, 593.1, DIG. 43, DIG. 47
See application file for complete search history.

(56) References Cited

U.S. PATENT DOCUMENTS

RE20,211 E * 12/1936 Motsinger
2,353,643 A 7/1944 Bulbulian
(Continued)

FOREIGN PATENT DOCUMENTS
DE 29723101 U1 7/1998
DE 19947722 4/2001
(Continued)

OTHER PUBLICATIONS

First Office Action for co-pending Chinese Application No. 201010185131.3, mailed Nov. 11, 2010, 9 pages.
(Continued)

*Primary Examiner* — Patricia Bianco
*Assistant Examiner* — Nihir Patel
(74) *Attorney, Agent, or Firm* — Nixon & Vanderhye P.C.

(57) ABSTRACT

A respiratory mask assembly for delivering breathable gas to a patient includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction which resists movement of the at least one strap of the pair of side straps in the first direction.

62 Claims, 16 Drawing Sheets

U.S. PATENT DOCUMENTS

| | | | |
|---|---|---|---|
| 4,099,524 | A | 7/1978 | Cueman et al. |
| 4,367,735 | A | 1/1983 | Dali et al. |
| 4,437,462 | A | 3/1984 | Piljay et al. |
| 4,593,688 | A | 6/1986 | Payton |
| 4,640,269 | A | 2/1987 | Goins |
| 5,117,819 | A | 6/1992 | Servidio et al. |
| D334,633 | S | 4/1993 | Rudolph |
| 5,233,978 | A | 8/1993 | Callaway |
| 5,284,469 | A | 2/1994 | Jasen et al. |
| 5,481,763 | A | 1/1996 | Brostrom et al. |
| 5,488,948 | A | 2/1996 | Dubruille et al. |
| 5,490,504 | A | 2/1996 | Vrona et al. |
| 5,517,986 | A | 5/1996 | Starr et al. |
| 5,529,062 | A | 6/1996 | Byrd et al. |
| 5,542,128 | A | 8/1996 | Lomas et al. |
| D383,204 | S | 9/1997 | Lomas |
| 5,771,886 | A | 6/1998 | Maire et al. |
| 5,806,516 | A | 9/1998 | Beattie |
| 5,840,050 | A | 11/1998 | Lerman |
| 5,921,239 | A | 7/1999 | McCall et al. |
| 5,924,421 | A | 7/1999 | Rosbrook et al. |
| 5,950,248 | A | 9/1999 | Kawashima et al. |
| 6,016,807 | A | 1/2000 | Lodge |
| 6,062,222 | A | 5/2000 | Lewis et al. |
| 6,105,573 | A | 8/2000 | Delaplane et al. |
| D433,127 | S | 10/2000 | Gazzara |
| 6,269,814 | B1 | 8/2001 | Blaszczykiewicz et al. |
| 6,338,342 | B1 | 1/2002 | Fecteau et al. |
| 6,374,826 | B1 | 4/2002 | Gunaratnam et al. |
| 6,422,238 | B1 | 7/2002 | Lithgow |
| 6,467,483 | B1 | 10/2002 | Kopacko et al. |
| 6,470,886 | B1 | 10/2002 | Jestrabek-Hart |
| 6,494,207 | B1 | 12/2002 | Kwok |
| 6,591,837 | B1 | 7/2003 | Byram |
| 6,732,733 | B1 | 5/2004 | Brostrom et al. |
| 6,772,760 | B2 | 8/2004 | Frater et al. |
| 7,188,620 | B2 | 3/2007 | Amarasinghe |
| 7,219,669 | B1 | 5/2007 | Lovell et al. |
| 7,509,958 | B2 * | 3/2009 | Amarasinghe et al. .. 128/206.24 |
| 7,802,573 | B2 | 9/2010 | Amarasinghe |
| 8,042,543 | B2 * | 10/2011 | Amarasinghe et al. .. 128/207.11 |
| 2002/0117177 | A1 | 8/2002 | Kwok |
| 2003/0196657 | A1 | 10/2003 | Ging et al. |
| 2004/0067333 | A1 | 4/2004 | Amarasinghe |
| 2004/0112377 | A1 | 6/2004 | Amarasinghe et al. |
| 2007/0169777 | A1 | 7/2007 | Amarasinghe |
| 2009/0038622 | A1 | 2/2009 | Amarasinghe et al. |
| 2010/0319688 | A1 | 12/2010 | Amarasinghe |

FOREIGN PATENT DOCUMENTS

| | | |
|---|---|---|
| EP | 0747078 A2 | 12/1996 |
| EP | 1 020 201 | 7/2000 |
| EP | 1 020 201 A2 | 7/2000 |
| EP | 2298410 | 3/2011 |
| FR | 2 618 340 A | 1/1989 |
| GB | 2 247 396 A | 3/1992 |
| JP | 52-36897 | 3/1977 |
| JP | 62-09460 | 1/1987 |
| JP | 8-57055 | 3/1996 |
| JP | 2000-254229 | 9/2000 |
| JP | 3076462 | 1/2001 |
| JP | 2002-537078 | 11/2002 |
| WO | WO 96/25983 | 8/1996 |
| WO | WO 96/28207 | 9/1996 |
| WO | WO 97/20597 | 6/1997 |
| WO | WO 98/48878 A2 | 11/1998 |
| WO | WO 00/50122 | 8/2000 |
| WO | WO 02/07806 A1 | 1/2002 |
| WO | WO 02/47749 A1 | 6/2002 |
| WO | WO 02/47763 A1 | 6/2002 |

OTHER PUBLICATIONS

Japanese Office Action and English translation for copending Japanese Application No. 2004-548920, mailed Mar. 16, 2010, 8 pages.
Office Action fro co-pending European Application No. 03810330.5, mailed Oct. 21, 2010, 6 pages.
PCT International Search Report for PCT/AU03/01161, dated Oct. 14, 2003.
Supplementary Search Report for co-pending European Application No. 03810330.5, mailed Jun. 25, 2010, 3 pages.
U.S. Appl. No. 10/390,681, filed Mar. 19, 2003.
U.S. Appl. No. 29/166,190, filed Aug. 9, 2002.
U.S. Appl. No. 60/377,254, filed May 3, 2002.
U.S. Appl. No. 60/397,195, filed Jul. 22, 2002.
U.S. Appl. No. 60/402,509, filed Aug. 12, 2002.
Letter to New Zealand Patent Office with Notice of Opposition and Extension Letter for corresponding New Zealand Patent Application No. 585295, dated Apr. 23, 2012, 4 pages.
Examination Report for corresponding New Zealand Application No. 595935, mailed Oct. 28, 2011, 2 pages.
European Patent Office Communication for corresponding EP Application No. 03 810 330.5-1257, mailed Sep. 28, 2012, 4 pages.
Notice of Opposition for corresponding New Zealand Patent Application No. 585295, dated May 30, 2012, 22 pages.
Notice of Reasons for Rejection and English Translation for corresponding Japanese Application No. 2010-205442, mailed Jun. 19, 2012, 7 pages.
New Zealand Examination Report for Patent Application No. 602732 dated Oct. 4, 2012, 2 pages.
Supplementary European Search Report for EP 01270356.7 mailed Feb. 3, 2006, 3 pages.
European Office Action for corresponding EP Application No. 01 270 356.7, mailed Jun. 11, 2007, 3 pages.
Extended European Search Report in EP 10 18 5034 dated Feb. 22, 2011, 6 pages.
Extended European Search Report in EP 10 18 5039 dated Feb. 16, 2011.
European Search Report for corresponding EP Appln. No. 10183627, mailed Mar. 1, 2011, 12 pages.

* cited by examiner

HEADGEAR ASSEMBLY FOR A RESPIRATORY MASK ASSEMBLY

CROSS-REFERENCE TO PRIORITY APPLICATIONS

This is a continuation of U.S. application Ser. No. 12/285,445, filed Oct. 6, 2008, now allowed, which is a continuation of U.S. application Ser. No. 10/655,602, filed Sep. 5, 2003, now U.S. Pat. No. 7,509,958, which claims priority to U.S. Provisional Application Ser. No. 60/424,694 filed Nov. 8, 2002, each incorporated herein by reference in its entirety.

FIELD OF THE INVENTION

The present invention relates to a headgear assembly for use in holding a respiratory mask assembly in position on a patient's face, the mask assembly being used for treatment, e.g., of Sleep Disordered Breathing (SDB) with Non-invasive Positive Pressure Ventilation (NPPV).

BACKGROUND OF THE INVENTION

Respiratory mask assemblies such as the Mirage® nasal mask assembly manufactured by RedMed Ltd. and used for treatment of SDB such as Obstructive Sleep Apnea (OSA) are typically held in position on a patient's head by a headgear assembly. A headgear assembly typically includes a pair of side portions and a rear portion. The side portions are adapted to engage with the patient's mask and the rear portion is adapted to engage the back of the patient's head.

Headgear assemblies are structured to position and stabilize a patient interface, such as a nasal mask, on a patient's face so that a good seal can be maintained. In addition, the headgear assembly should be comfortable so that a patient can wear the mask assembly at night while they sleep. Many prior art headgear assemblies are uncomfortable to wear for long periods. It is desirable that one form of headgear assembly is suitable for a broad range of patients in order to reduce inventory, and ultimately reduce costs.

Completely rigid headgear assemblies are known, but they typically suffer from being uncomfortable to wear for long periods. In addition, because of their rigidity, they typically do not fit a broad range of patients, being suitable only for a subset.

For reasons of costs, it is desirable to be able to cut headgear assemblies from a flat piece of fabric or composite, yet in use the headgear assembly should conform to a complex three-dimensional shape. Hence a problem to overcome is to have a design of headgear assembly which can be easily manufactured by cutting or stamping, and yet in use be able to fit a wide range of head shapes and sizes.

Known forms of headgear assemblies include the ResCap™, ResCap™ II and MIRAGE® headgear, as shown in FIGS. 11-16. These headgear assemblies are constructed from fabric or composite layers of fabric and neoprene. Because of the soft flexible nature of the straps in the headgear assembly, there is the possibility of some movement of the headgear assembly on the patient's head, particularly during the course of a night's sleep. Hence, while the headgear assembly may be initially correctly positioned on a patient's head, they may subsequently move to an incorrect position.

A form of connector to enable the headgear assembly to engage with the patient's mask is taught in U.S. Pat. No. 6,374,826 (Gunaratnam et al.), the contents of which are hereby incorporated by reference.

U.S. Pat. No. 6,422,238 (Lithgow) shows a form of headgear assembly including a quick-release mechanism. The contents of the Lithgow patent are hereby incorporated by reference. The headgear assembly taught by Lithgow includes an upper and lower strap in each side portion extending between the patient's face and the rear of the patient's head. The upper straps lie above the ears on the patient's head. The lower straps lie below the ears on the patient's head.

A problem which can occur with prior art mask assemblies, such as the mask assemblies shown in FIGS. 11-16 and taught by Gunaratnam and Lithgow, is that the lower straps of the mask assemblies can ride up the patient's head while in use and cause chafing and irritation of the lower portion of the patient's ears.

SUMMARY OF THE INVENTION

One aspect of the present invention is directed towards a mask assembly having a headgear assembly that offers more comfort to the patient yet does not sacrifice functionality.

Another aspect of the present invention provides a respiratory mask assembly for delivering breathable gas to a patient. The respiratory mask assembly according to one embodiment includes a frame and a headgear assembly removably attachable to the frame. The headgear assembly includes a pair of side portions and a rear portion that interconnects the pair of side portions. The pair of side portions includes at least one strap. The rear portion has at least one strap constructed of at least two layers of material. One of the layers of material has a more rigid construction than the other of the layers of material to resist compression of the at least one strap of the rear portion in a first direction and thereby resist movement of the at least one strap of the pair of side straps in the first direction.

Another aspect of the invention is to provide a means for maintaining flexible headgear straps of a mask assembly in correct relative position on a patient's head in use.

Another aspect of the invention is to provide a comfortable headgear assembly for a mask assembly which fits a wide range of head shapes and sizes.

Another aspect of the invention is to provide a comfortable headgear assembly of a mask assembly which fits a wide range of patients and can be cut from a flat piece of fabric.

Other aspects, features and advantages of this invention will become apparent from the following detailed description when taken in conjunction with the accompanying drawings, which are part of this disclosure and which illustrate, by way of example, principles of this invention.

BRIEF DESCRIPTION OF THE DRAWINGS

The accompanying drawings facilitate an understanding of the various embodiments of this invention. In such drawings.

DETAILED DESCRIPTION OF ILLUSTRATED EMBODIMENTS

Figure 1:
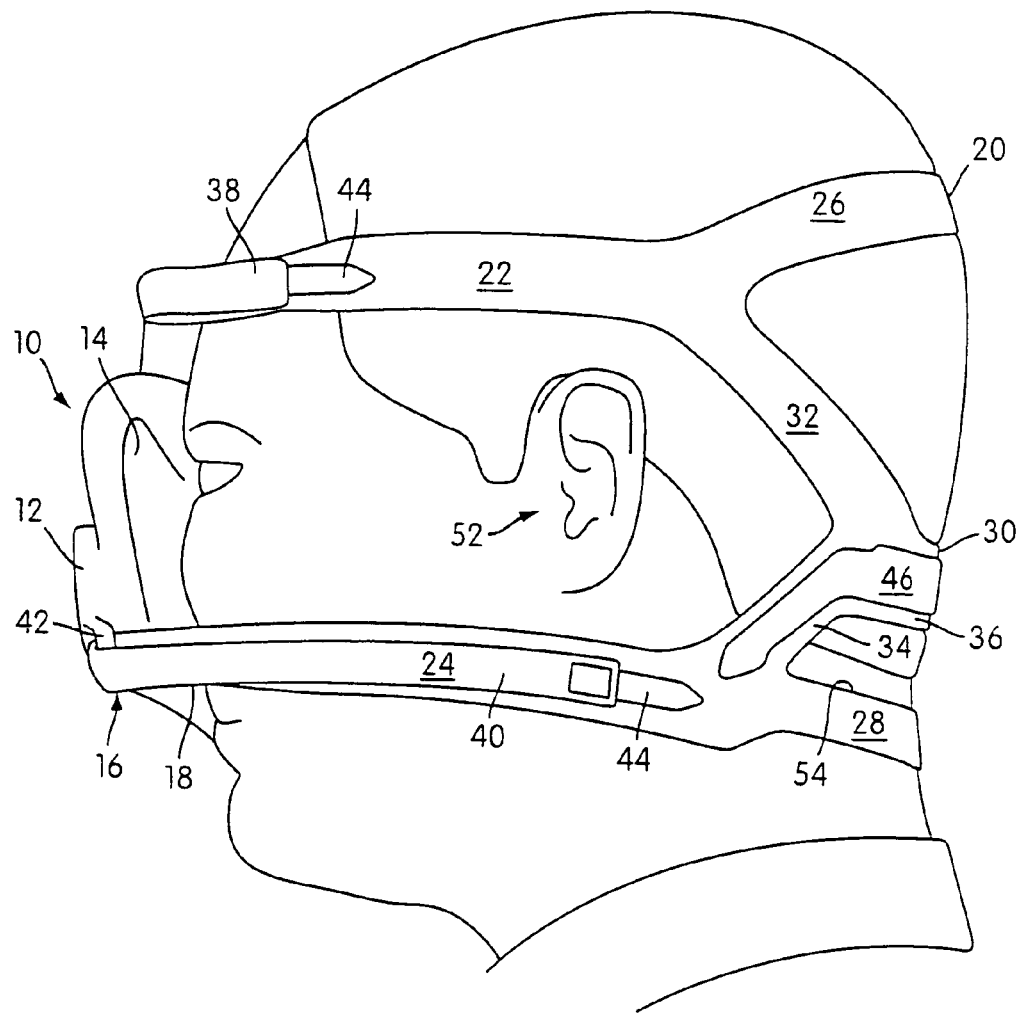
FIG. 1 is a side view illustrating a mask assembly having a headgear assembly constructed in accordance with an embodiment of the invention mounted on a patient's head.

FIG. 1 shows a respiratory mask assembly 10 that includes a frame 12 and a cushion 14 that may be permanently or removably connected to the frame 12. A headgear assembly 16 is removably attached to the frame 12 and is structured to maintain the frame 12 and cushion 14 in a desired adjusted position on a patient's face. In the illustrated embodiment, the mask assembly 10 is a nasal mask structured to deliver breathable gas to a patient's nose. However, the mask assembly 10 may be a nasal and mouth mask or the mask assembly 10 may be a full-face mask.

As shown in FIGS. 1-4, the headgear assembly 16 includes two side portions 18 with a rear portion 20 connecting the side portions 18. Each side portion 18 comprises an upper side strap 22 and a lower side strap 24. The rear portion 20, which interconnects the two side portions 18, includes a curved upper strap 26, a lower strap 28, and an intermediate strap arrangement 30 therebetween. The intermediate strap arrangement 30 is generally H-shaped and has a pair of upper straps 32, a pair of lower straps 34, and a cross-bar strap 36. The upper straps 32 are angled with respect to the curved upper strap 26 and the lower straps 34 are angled with respect to the lower strap 28. However, the straps of the headgear assembly 16 may have any suitable configuration to maintain the frame 12 and cushion 14 in a desired adjusted position on a patient's face. For example, the upper strap 26 may not be curved with respect to the upper straps 22 and the intermediate strap arrangement 30 may have any suitable shape, i.e., not H-shaped.

Figure 4:
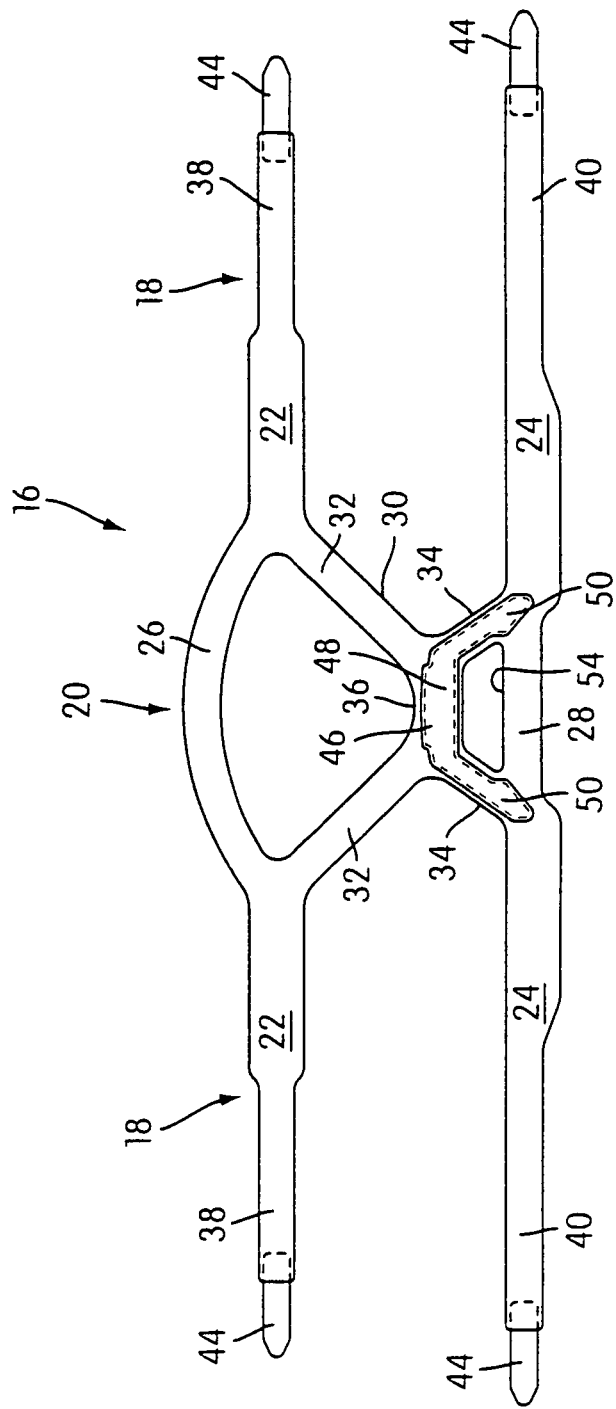
FIG. 4 is a top view illustrating the headgear assembly of FIG. 1 laid flat.

Each upper side strap 22 is removably connected to an upper portion of the frame 12 and each lower side strap 24 is removably connected to a lower portion of the frame 12. As shown in FIG. 4, the end portion 38, 40 of each upper and lower strap 22, 24, respectively, has a reduced width that enables each upper and lower strap 22, 24 to be wrapped around a respective clip structure 42 (see FIG. 1) provided on the frame 12. Fastening of the upper and lower straps 22, 24 to the frame 12 may be assisted by use of a hook and loop material, such as VELCRO®. As shown in FIG. 4, the free end of each upper and lower strap 22, 24 includes a strip of hook material 44 attached thereto by stitching, for example.

The upper and lower straps 22, 24 are constructed of a loop material that engages the strip of hook material 44 when the upper and lower straps 22, 24 are connected to the frame 12.

However, the upper and lower straps 22, 24 may be connected to the frame 12 in any other suitable manner. For example, the upper and lower straps 22, 24 may include locking clips attached thereto that are adapted to interlockingly engage with the frame 12. Alternatively, the upper and lower straps 22, 24 may be magnetically coupled with the frame 12 so as to interconnect the frame 12 and headgear assembly 16. Further, the frame 12 may include a forehead support movably mounted to an upper portion thereof. In such an arrangement, the upper straps 22 may be removably connected to clip structures provided on the forehead support.

Figure 7:
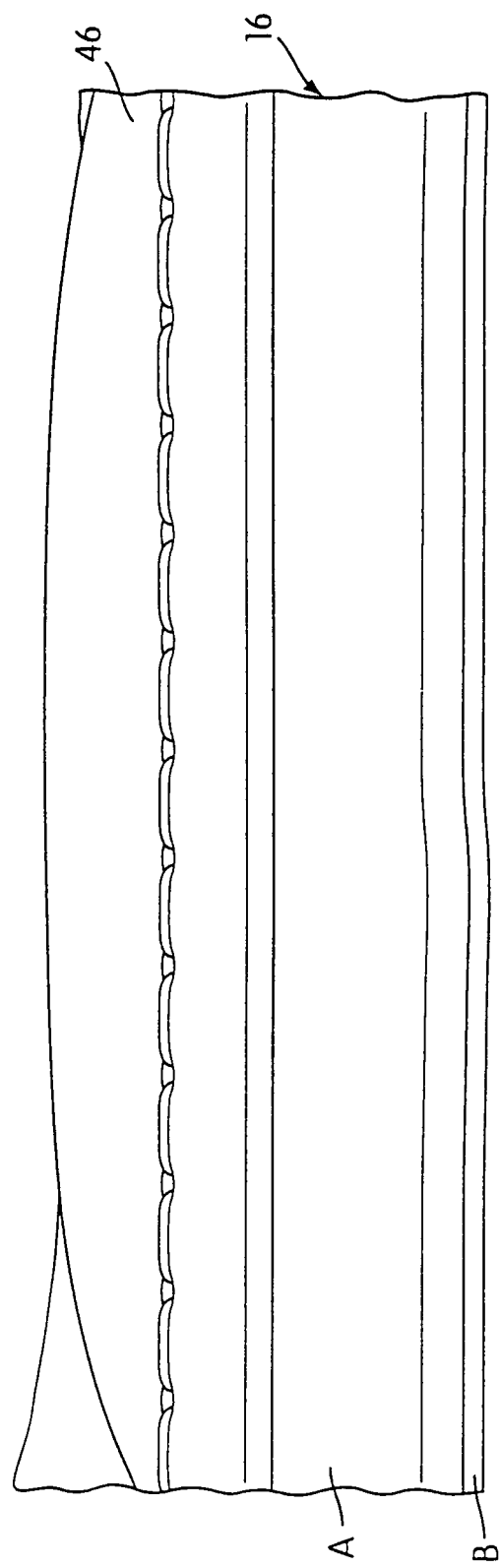
FIG. 7 is an enlarged photographic side view illustrating an embodiment of a stiffener of the headgear assembly of FIG. 1.

The straps of the headgear assembly 16 are constructed from a soft, flexible composite material such as Breathe-O-Prene™ manufactured by Accumed Technologies, Inc. As shown in FIG. 7, the straps include two layers of material A, B with one of the layers A having a loop material to facilitate the connection with the strip of hook material 44 provided on the free ends the upper and lower straps 22, 24. However, the straps may be constructed from any other suitable soft, flexible material.

In the illustrated embodiment, a stiffener 46 is attached to the rear portion 20 of the headgear assembly 16. As shown in FIGS. 2 and 4-6, the stiffener 46 has a general C-shape including a body 48 and a pair of arm members 50. The stiffener 46 is attached to the H-shaped intermediate strap arrangement 30 such that the body 48 of the stiffener 46 extends along the cross-bar strap 36 and the arm members 50 of the stiffener 46 extend along respective lower straps 34. The body 48 has a width that is greater than a width of the arm members 50. Further, the free ends of the arm members 50 have a greater width than the remaining portion of the arm members 50. However, the stiffener 46 may have any suitable structure and width dimensions. The stiffener 46 is constructed from a semi-rigid skin-compatible material such as thermoplastics, e.g., nylon or polyester or a thermoplastic elastomer, e.g. santoprene. The stiffener 46 has a thickness in the range of 0.8 mm to 1.5 mm, preferably 1 mm.

Figure 5:
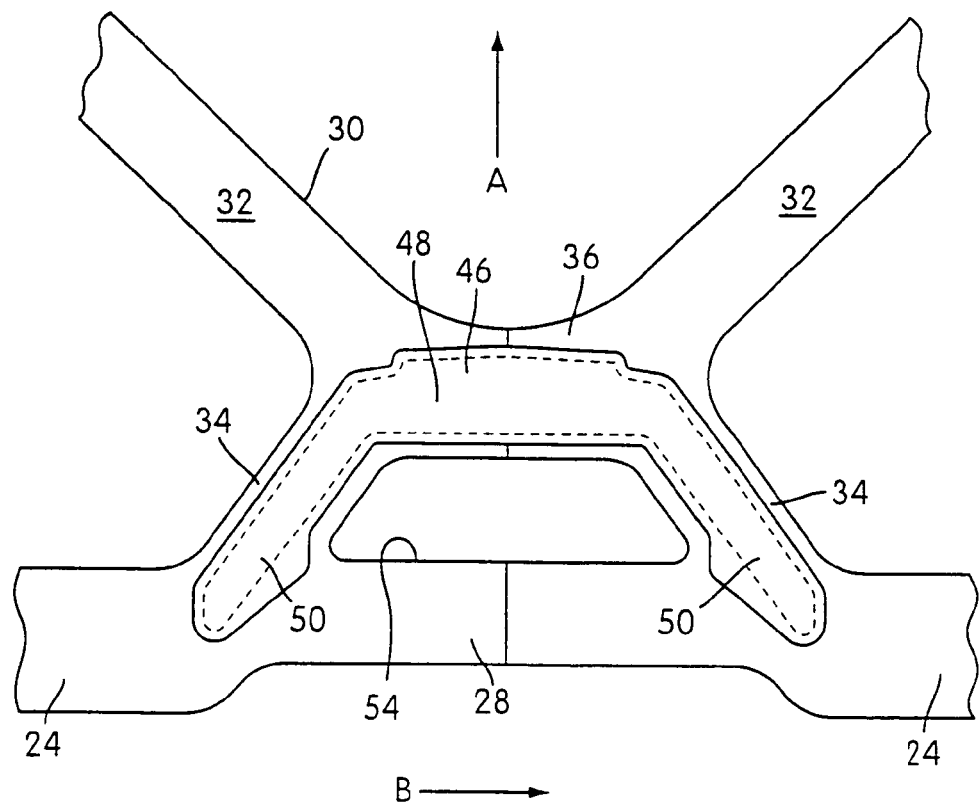
FIG. 5 is an enlarged top view illustrating an embodiment of a stiffener of the headgear assembly of FIG. 1.
Figure 6:
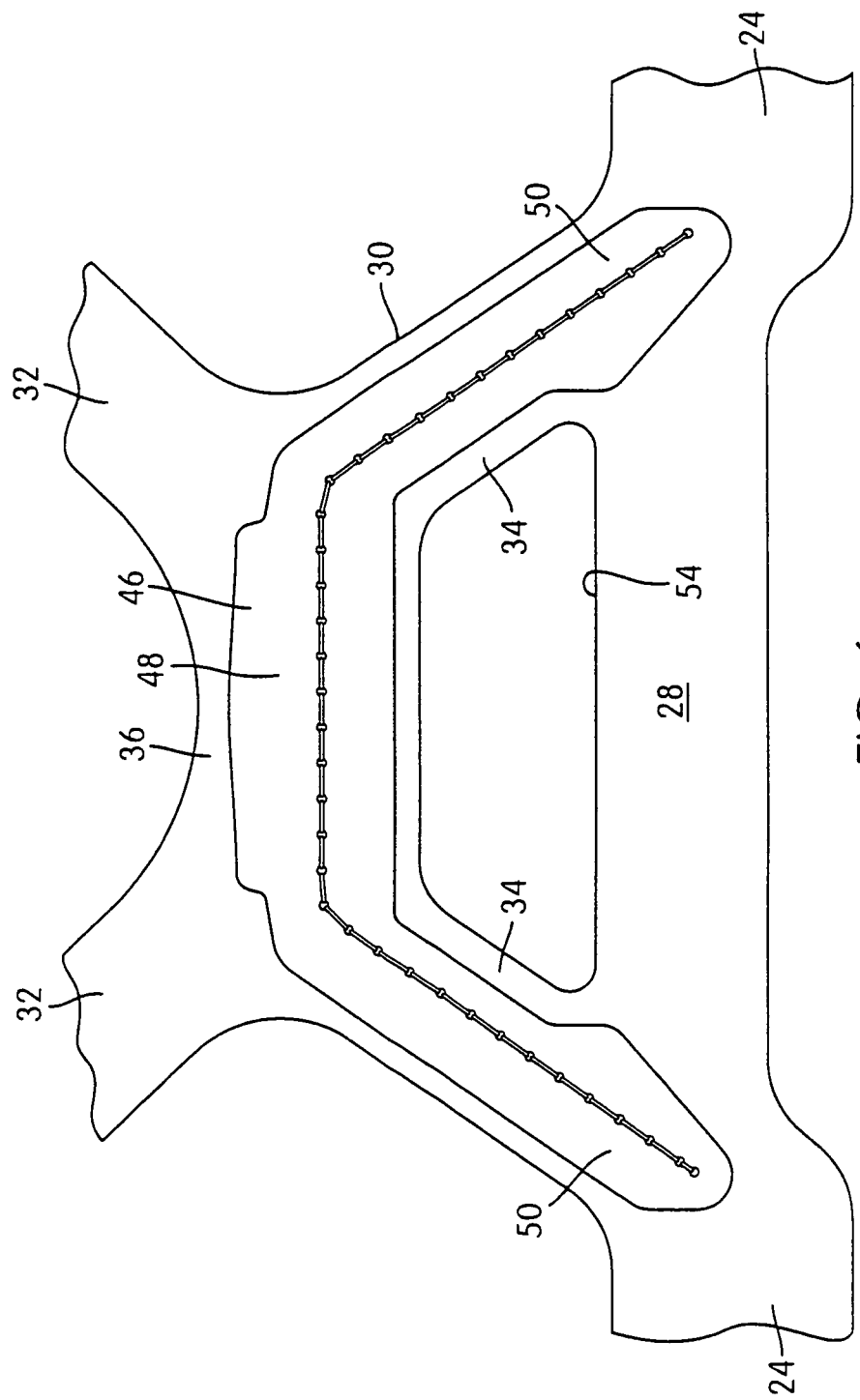
FIG. 6 is an enlarged photographic top view illustrating an embodiment of a stiffener of the headgear assembly of FIG. 1.

The stiffener 46 is attached to the corresponding straps 34, 36 with adhesives, stitching, or other known attachment mechanisms or by semi-permanent means such as velcro, pocket sleeve, etc. As shown in FIG. 5, the stiffener 46 is secured to the straps 34, 36 by stitching around the periphery of the stiffener 46. As shown in FIG. 6, the stiffener 46 is secured to the straps by stitching an intermediate portion of the stiffener 46. FIG. 7 is an enlarged view that illustrates the stiffener 46 secured to the straps by stitching. The stitch line is in the range of 2-3 mm, preferably 2.5 mm, from the edge of the stiffener 46.

The stiffener 46 is narrower than the straps 34, 36 so that when the stiffener 46 is attached to the straps 34, 36, the softer material of the straps 34, 36 extends beyond the more rigid material of the stiffener 46, thereby preventing or at least reducing the opportunity for contact between the patient and the more rigid material of the stiffener 46 that could cause irritation or discomfort.

The stiffener 46 adds to the rigidity of the headgear assembly 16 in certain planes and directions, which assists in stabilizing the mask assembly 10 on the head of the patient during use. In other planes and directions, the headgear assembly 16 has a different rigidity.

Figure 2:
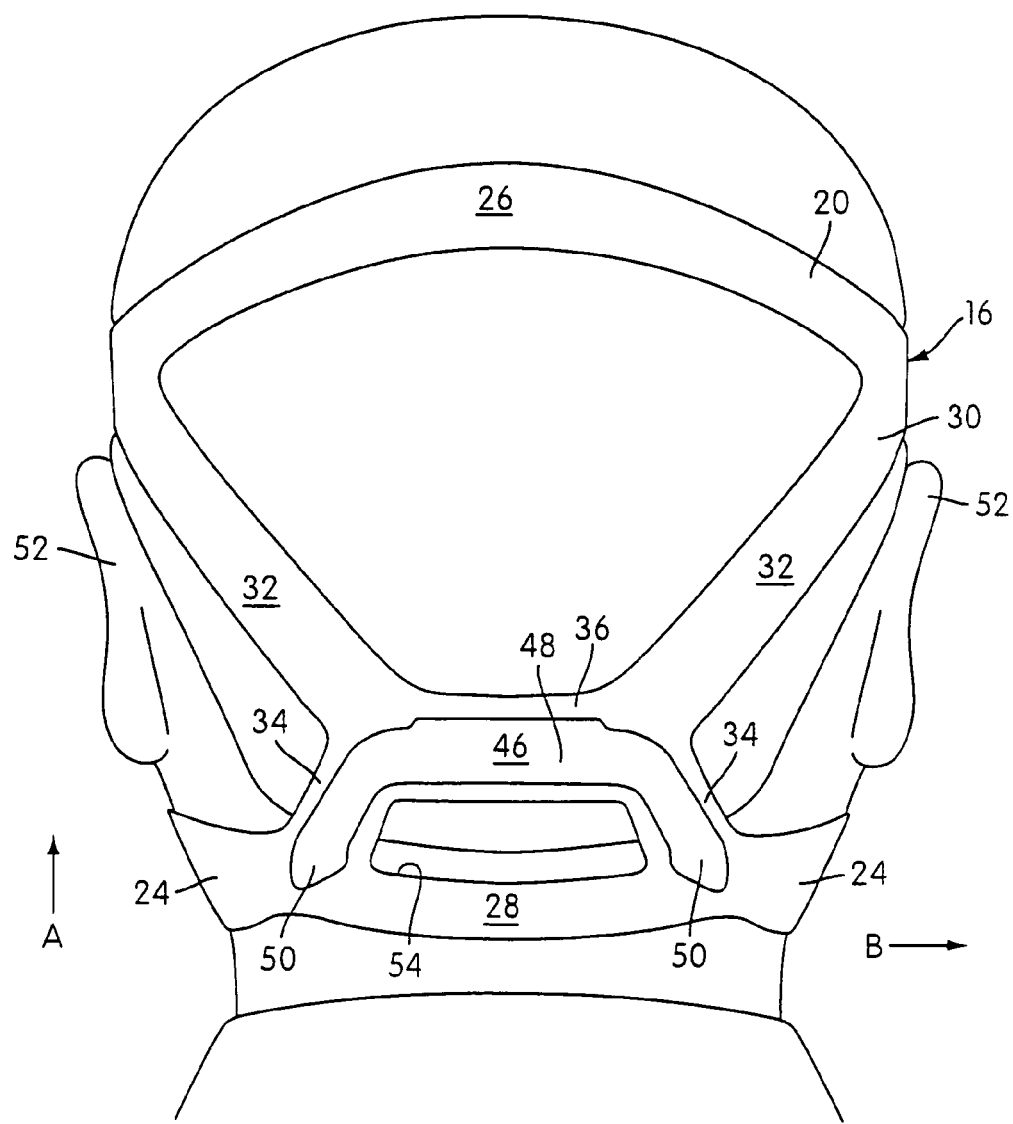
FIG. 2 is a rear view illustrating the headgear assembly of FIG. 1 mounted on a patient's head.
Figure 3:
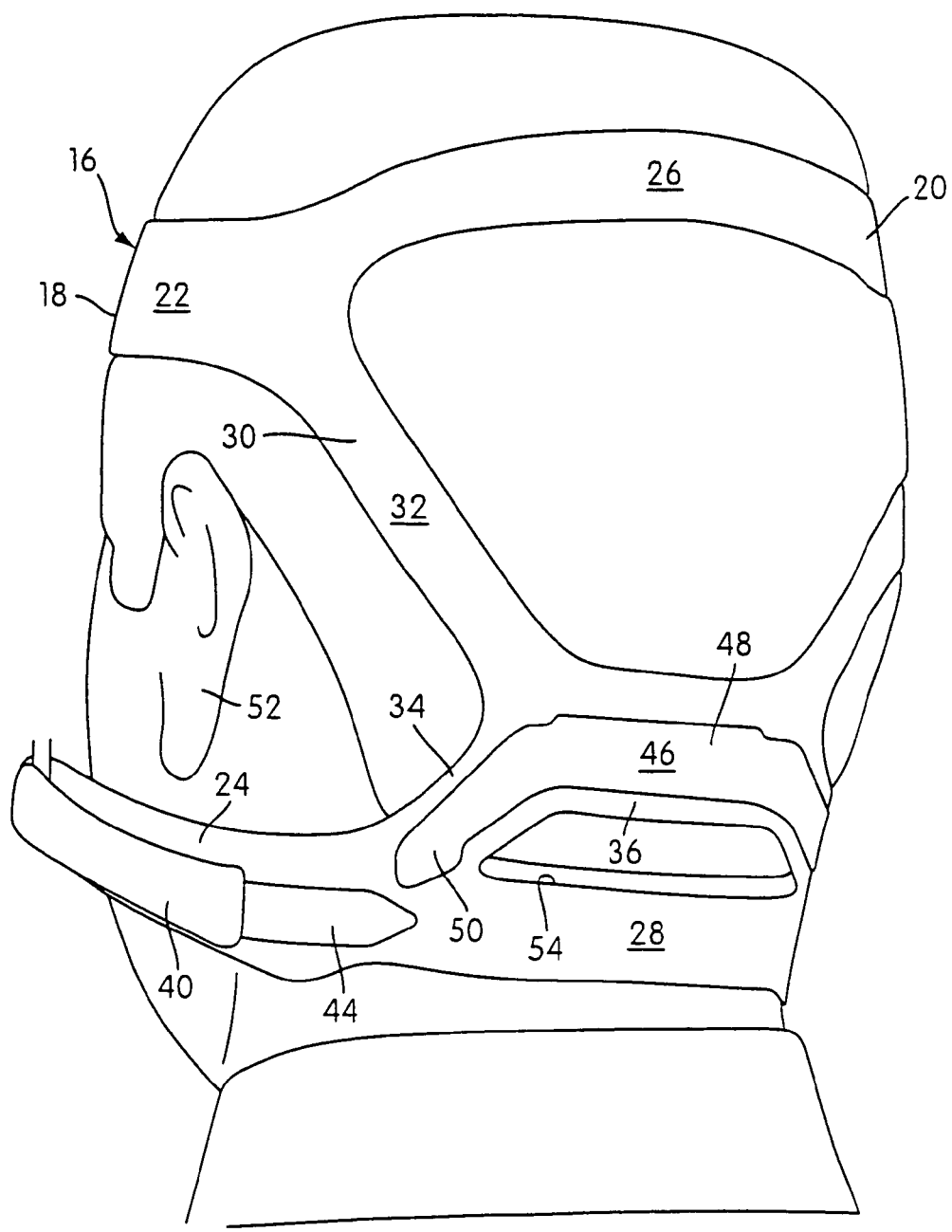
FIG. 3 is a rear perspective view illustrating the headgear assembly of FIG. 1 mounted on a patient's head.

For example, the stiffener 46 reduces the flexibility of the straps 34, 36 at the back of the patient's head along the direction of arrow A or in a reverse direction of arrow A, as shown in FIG. 2. The presence of the stiffener 46 stops compression of the straps 34, 36 along the reverse direction of arrow A. In this way, the straps 34, 36 and stiffener 46 should be able to resist the riding up of the lower straps 24 towards the patient's ears 52. In general, the straps 34, 36 and stiffener 46 should be able maintain their positions with respect to the head of the patient when the straps 34, 36 and stiffener 46 are connected to the frame 12. Thus, the likelihood that the lower straps 24 will ride up into the lower portion of the ears 52 of the patient is reduced.

Further, the headgear assembly 16 is shaped to avoid interference with the patient's ears 52. In particular, the upper side strap 22 is connected to the frame 12 above the patient's eyes and patient's ears 52. The lower side strap 24 is connected to the frame 12 and extends below the patient's ear 52. The upper straps 32 and lower straps 34 interconnect the upper and lower straps 22, 24 and are angled sufficiently away from the patient's ears 52. Also, the upper and lower straps 32, 34 are of sufficient length to space the upper and lower straps 22, 24 from the patient's ears 52. Due to the added rigidity provided by the stiffener 46, all the straps of the headgear assembly 16 are better able to maintain a predetermined shape. The thickness of the stiffener 46 may vary across its profile to modify flexibility characteristics, for example, thicker regions may be stiffer.

On the other hand, a certain degree of flexibility of the headgear assembly 16 is provided such that variations in patient physiology can be accommodated to a certain degree. For example, the lower strap 28 has relatively more flexibility along arrow direction B or its reverse direction than straps 34, 36 with the stiffener 46 attached.

The H-shaped intermediate strap arrangement 30 of the headgear assembly 16 also helps maintain the headgear assembly 16 in a desired adjusted position on the patient. As shown in FIG. 1, the curved upper strap 26 extends across a rear upper portion of the patient's head and the lower strap 28 and cross-bar strap 36 extend across a rear lower portion of the patient's neck and head, respectively. More specifically, the curved upper strap 26 is structured to engage a posterior portion of the parietal bone of the patient's head in order to prevent downward movement of the headgear assembly 16 opposite the direction of arrow A in FIG. 2. The cross-bar strap 36 is structured to engage a lower portion of the occipital bone of the patient's head and the lower strap 28 is structured to engage a rear upper portion of the patient's neck. As a result, the cross-bar strap 36 and the lower strap 28 prevent upward movement of the headgear assembly 16 in the direction of arrow A in FIG. 2. Moreover, the stiffener 46 is structured to resist the riding up of the lower straps 34 and hence the lower straps 24 towards the patient's ears 52. However, the intermediate strap arrangement 30 may have any suitable configuration to maintain the frame 12 and cushion 14 in a desired adjusted position on a patient's face.

Further, the straps 28, 34, and 36 form an opening 54 therebetween that can accommodate any skin folds of a patient which may extend through the opening 54. Specifically, movement of the patient's head can create a fold of skin adjacent the patient's neck. The straps 28, 34, and 36 are structured and positioned on the patient's head such that any skin folds will extend through the opening 54 and not adversely affect the positioning of the headgear assembly 16 on the patient's head. The opening 54 formed between the straps 28, 34, and 36 may have any suitable shape, i.e., trapezoidal or non-trapezoidal shape. The reduced width of strap 28 allows it to stretch over the fatter lower neck, that is, there is a different stretch between strap 36 and strap 28.

Figure 8:
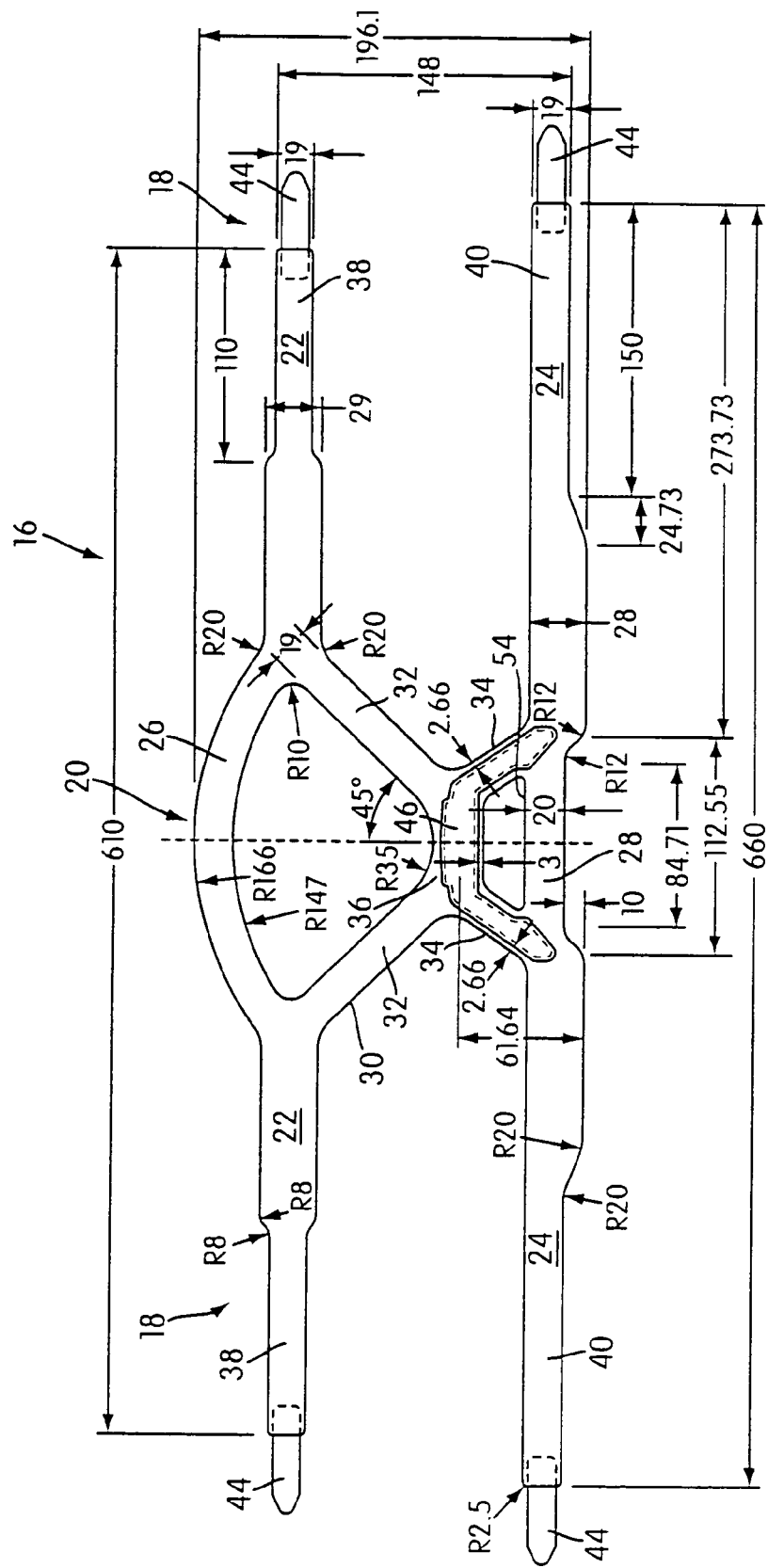
FIG. 8 is a top view illustrating the headgear assembly of FIG. 1 laid flat and showing typical dimensions of an embodiment (R-radius)

FIG. 8 illustrates dimensions of an embodiment of the headgear assembly 16. For example, the overall length of the headgear assembly 16 is in the range of 640-680 mm, preferably 660 mm and the overall height of the headgear assembly 16 is in the range of 175-215 mm, preferably 196.1 mm. The upper straps 32 are angled in the range of 40-50°, preferably 45°, with respect to the upper straps 22 and have a width in the range of 16-22 mm, preferably 19 mm. The curved upper strap 26 has a radius of curvature in the range of 145-170 mm, preferably 166 mm. Further, the lower strap 28 has a width in the range of 17-23 mm, preferably 20 mm, and the end portions 38, 40 of the upper and lower straps 22, 24 have a width in the range of 16-23 mm, preferably 19 mm. In an embodiment of the headgear assembly 16, the dimensions illustrated in FIG. 8 vary ±10%.

Figure 9:
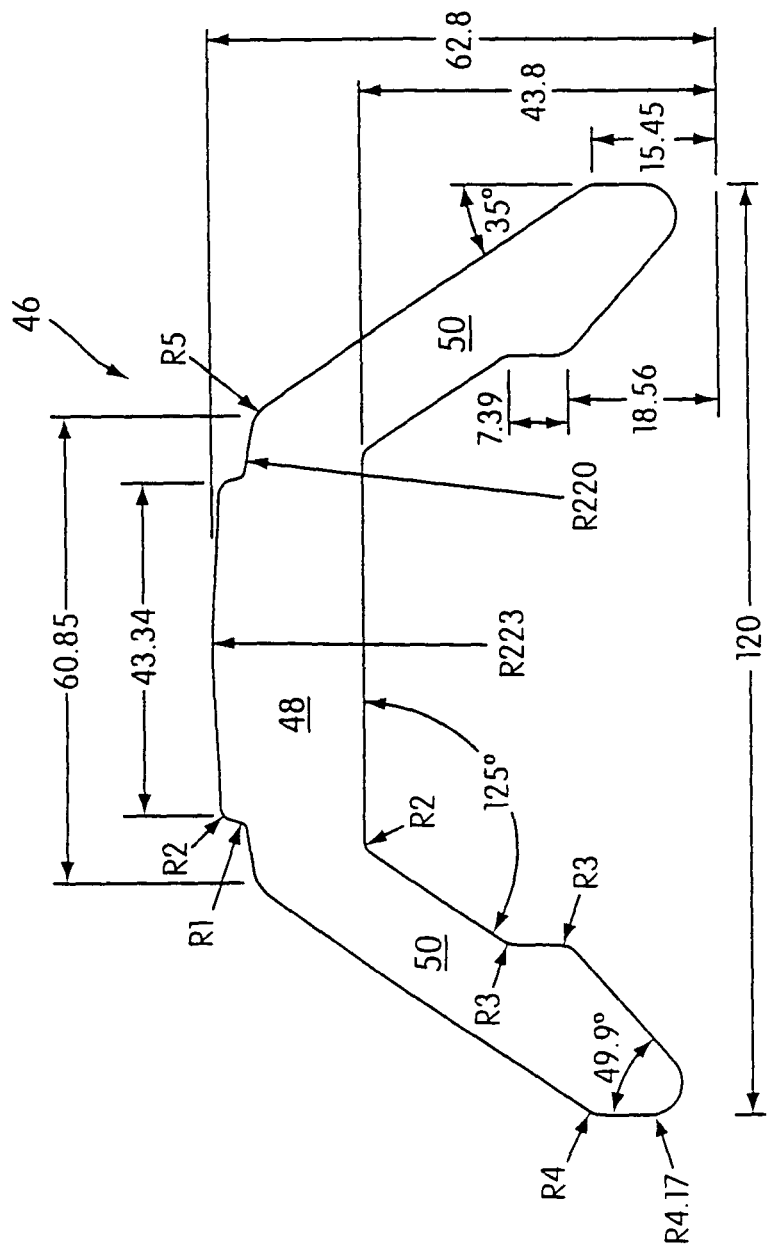
FIG. 9 is a top view illustrating an embodiment of a stiffener of the headgear assembly of FIG. 1 and showing typical dimensions of an embodiment (R-radius)

FIG. 9 illustrates dimensions of an embodiment of the stiffener 46. For example, the overall length of the stiffener 46 is in the range of 100-140 mm, preferably 120 mm and the overall height of the stiffener 46 is in the range of 40-80 mm, preferably 62.8 mm. The arm members 50 are angled in the range of 110-140°, preferably 125°, with respect to the body 48. In an embodiment of the stiffener 46, the dimensions illustrated in FIG. 9 vary ±10%.

Figure 10:
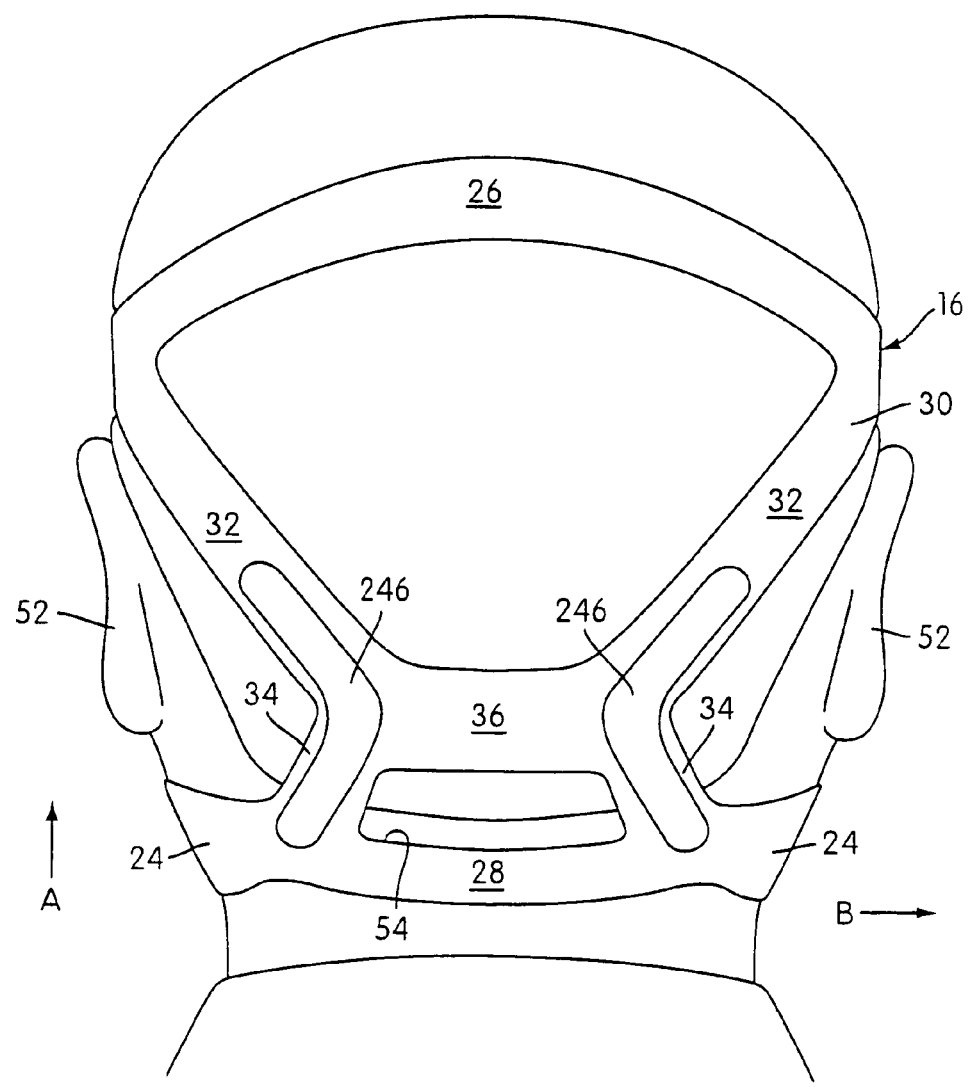
FIG. 10 is a rear view illustrating a headgear assembly constructed in accordance with another embodiment of the invention mounted on a patient's head.
Figure 11:
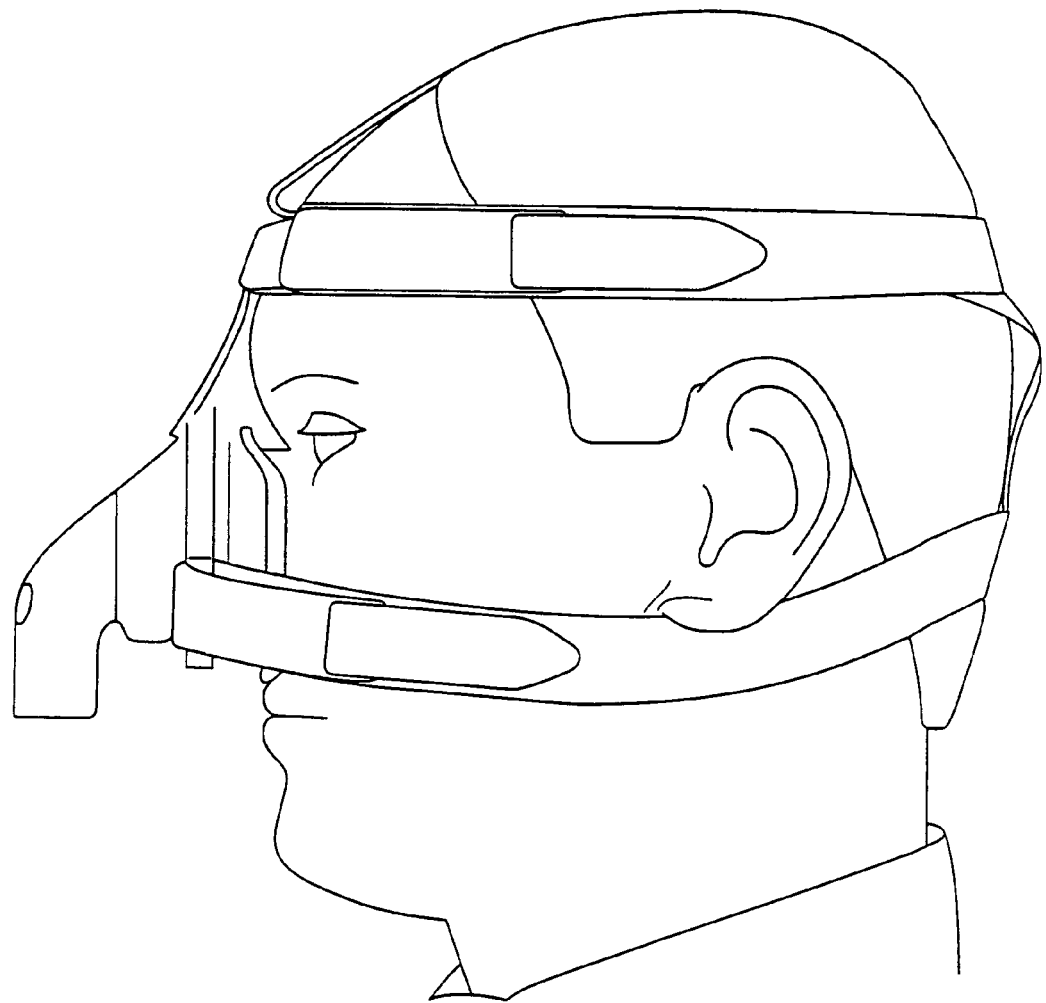
FIG. 11 is a side view of a prior art ResCap™ headgear assembly.
Figure 12:
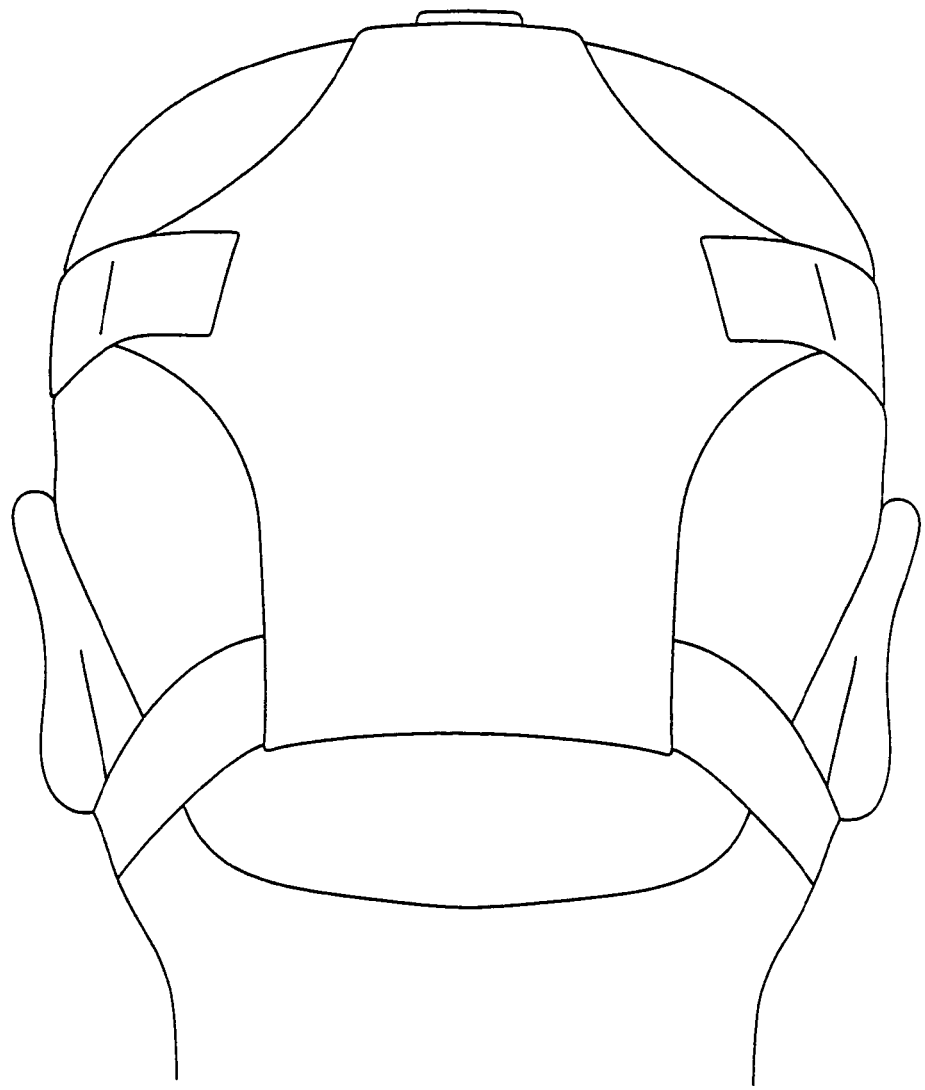
FIG. 12 is a rear view of a prior art ResCap™ headgear assembly.
Figure 13:
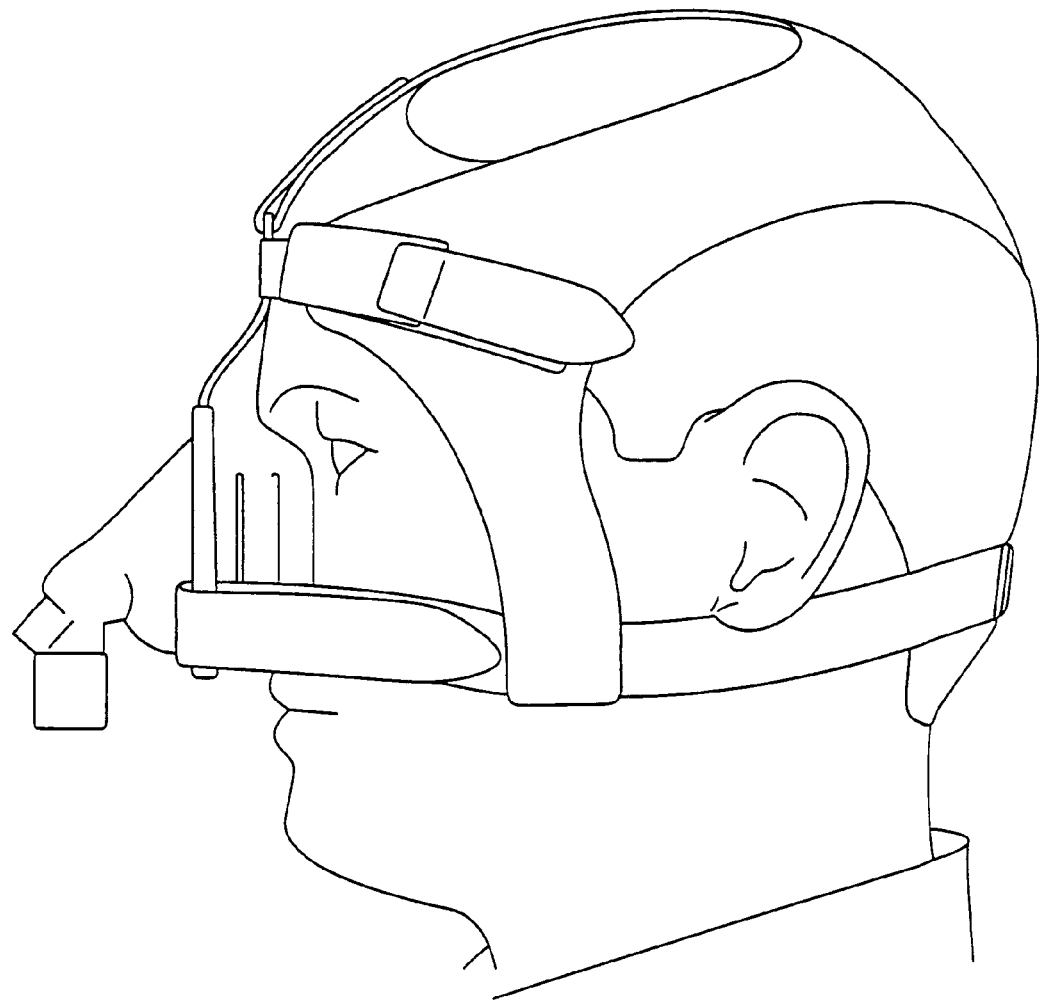
FIG. 13 is a side view of a prior art ResCap™ II headgear assembly.
Figure 14:
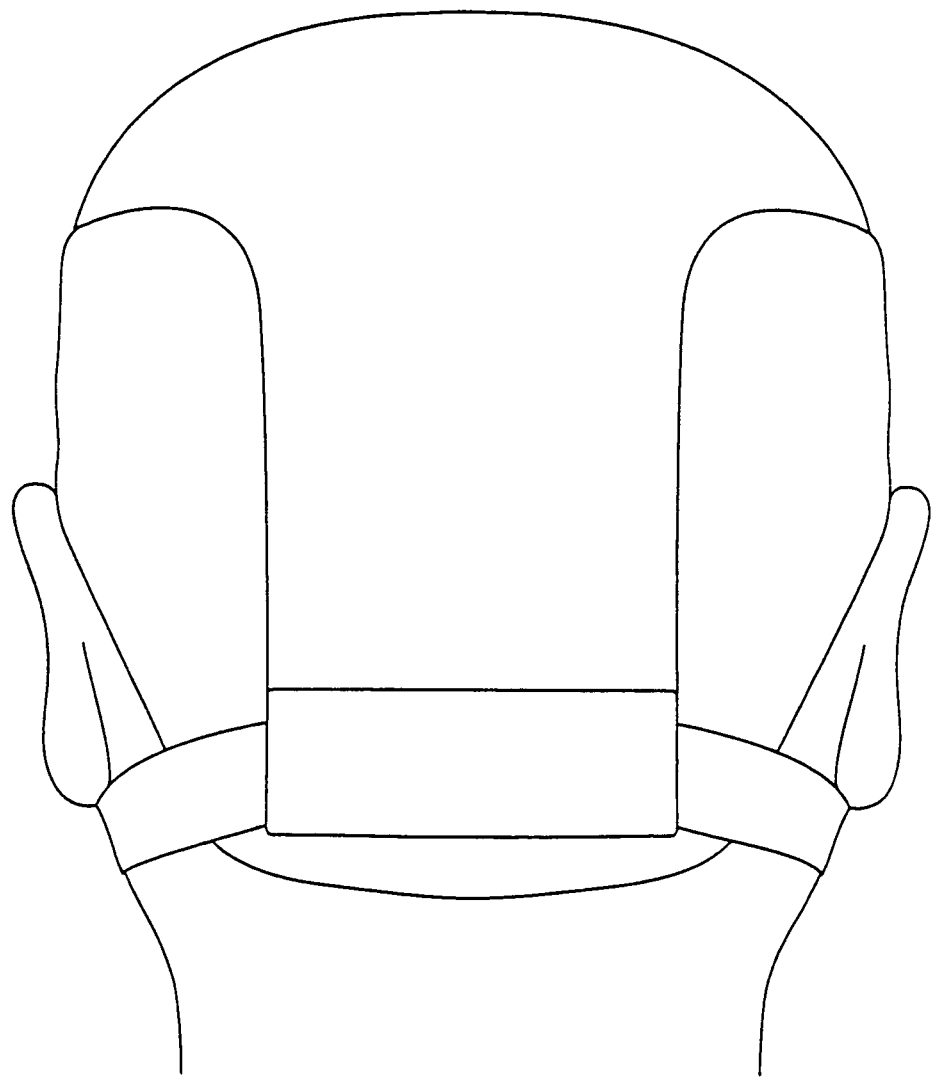
FIG. 14 is a rear view of a prior art ResCap™ II headgear assembly.
Figure 15:
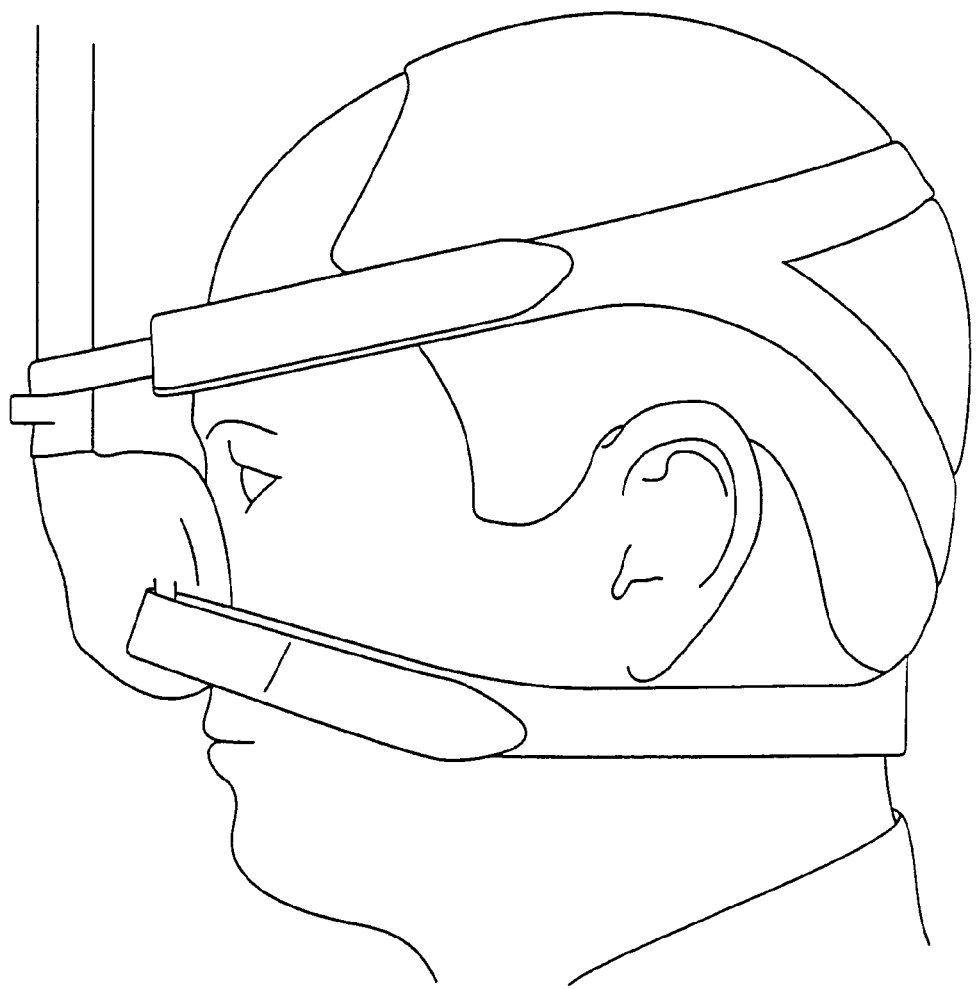
FIG. 15 is a side view of a prior art MIRAGE® headgear assembly.
Figure 16:
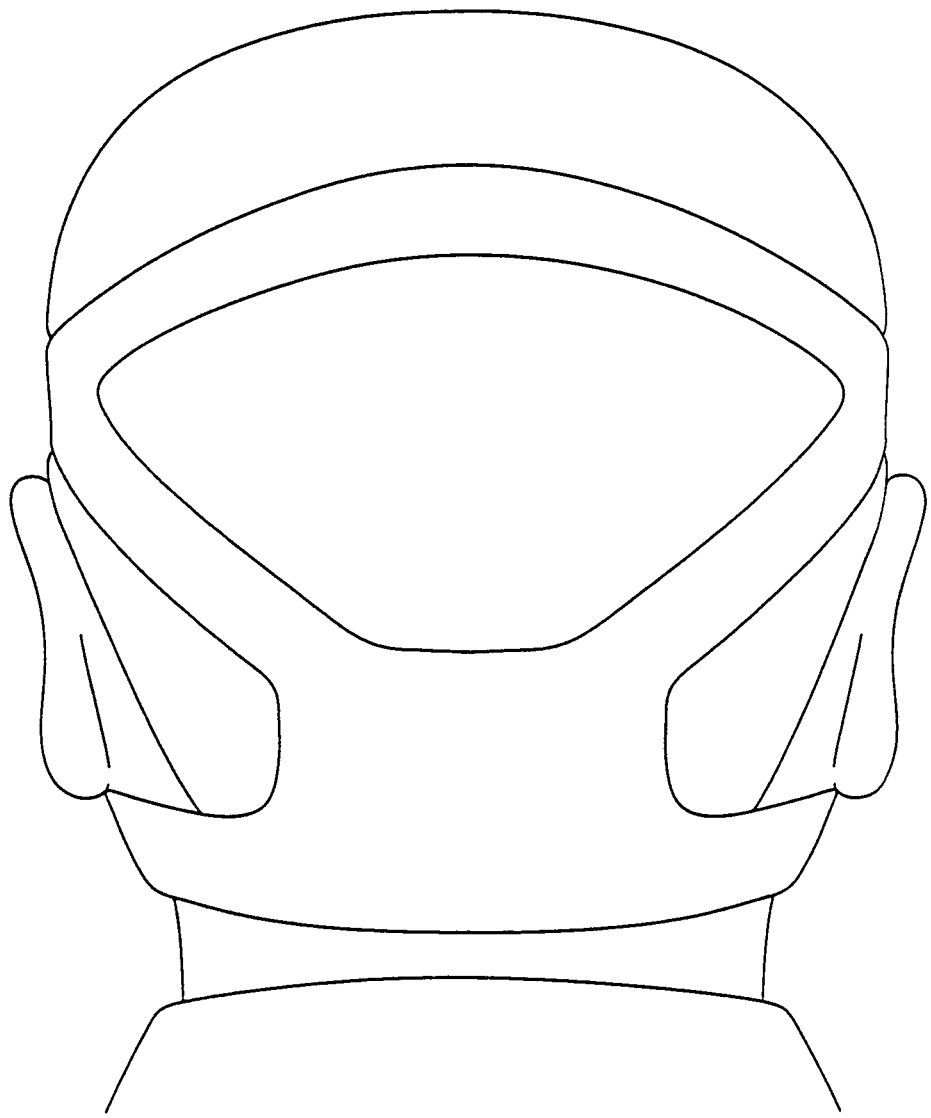
FIG. 16 is a rear view of a prior art MIRAGE® headgear assembly.

FIG. 10 illustrates another embodiment of the stiffener, indicated as 246. In this embodiment, the stiffener is in the form of a pair of arcuate-shaped stiffeners 246. Each stiffener 246 extends along the upper strap 32, across the cross-bar strap 36, and along the lower strap 34. Similar to the stiffener 46, the stiffeners 246 reduces the flexibility of the straps 32, 34, and 36 at the back of the patient's head along the direction of arrow A or in a reverse direction of arrow A, so as to resist the riding up of the lower straps 24 towards the patient's ears 52.

The straps of the headgear assembly 16 and the stiffener 46, 246 may be formed of a single material, so long as patient comfort and the appropriate rigidity/flexibility are maintained.

It can thus be appreciated that the aspects of the present invention have been fully and effectively accomplished. The foregoing specific embodiments have been provided to illustrate the structural and functional principles of the present invention, and are not intended to be limiting. To the contrary, the present invention is intended to encompass all modification, alterations and substitutions within the spirit and scope of the detailed description.

What is claimed is:

1. A headgear for attachment to a frame of a respiratory mask assembly to deliver breathable gas to a patient, comprising:
    a pair of side portions; and
    a rear portion that interconnects the pair of side portions, wherein: each of the pair of side portions includes an upper strap removably attachable to an upper portion of the frame and a lower strap assembly removably attachable to a lower portion of the frame, the upper strap being adapted to extend above the patient's ear, the rear portion includes an upper strap, a lower strap, and an intermediate strap arrangement between the upper and lower straps of the rear portion;
    wherein the intermediate straps arrangement includes a pair of upper straps angled with respect to the upper strap of the rear portion, a pair of lower straps angled with respect to the lower straps of the rear portion; and
    the pair of side portions and rear portions comprise a one-piece composite of soft, flexible material.

2. The headgear according to claim 1, wherein the intermediate strap arrangement further includes a cross-bar strap that extends between the upper and lower straps of the intermediate strap arrangement.

3. The headgear assembly according to claim 2, wherein the cross-bar strap of the intermediate strap arrangement, the pair of lower straps of the intermediate strap arrangement, and the lower strap of the rear portion define an opening therebetween that is adapted to allow folds of the patient's skin to extend therethrough.

4. A headgear assembly to stabilize and position a respiratory mask assembly on a patient's head, comprising:
   a pair of upper side straps and a pair of lower side straps, each strap having a distal free end;
   two rear straps including an upper rear strap and a lower rear strap; an intermediate strap arrangement positioned between the two rear straps, wherein the intermediate strap arrangement includes a pair of upper intermediate straps angled relative to the upper rear strap and a pair of lower intermediate straps angled relative to the lower rear strap;
   wherein the upper rear strap comprises a curved portion of a predetermined radius, wherein the predetermined radius is measured when the headgear assembly is laid out flat, and
   wherein the curved portion extends between and connects to the upper intermediate straps.

5. The headgear assembly according to claim 4, wherein the curved portion is structured to engage a posterior portion of the parietal bone of the patient's head in use.

6. The headgear assembly according to claim 4, wherein the pair of upper intermediate and lower intermediate straps converge towards and join with a cross bar strap.

7. The headgear assembly according to claim 4, wherein the pair of upper intermediate straps of the intermediate strap arrangement and the upper rear strap at least partially define a first opening.

8. The headgear assembly according to claim 7, wherein the lower rear strap and the pair of lower intermediate straps of the intermediate strap arrangement at least partially define a second opening.

9. The headgear assembly according to claim 7, wherein the first opening is substantially triangular.

10. The headgear assembly according to claim 8, wherein the second opening is substantially triangular.

11. A respiratory mask assembly to deliver a breathable gas to a patient, comprising:
    a mask frame and an adjustable forehead support; and
    the headgear assembly of claim 4.

12. The headgear assembly according to claim 4, wherein the upper side straps, lower side straps, rear straps, and intermediate strap arrangement comprise a one-piece composite material.

13. The headgear assembly according to claim 12, wherein an outer layer of the one-piece composite material is a loop material to facilitate a hook-and-loop connection.

14. The headgear assembly according to claim 13, further comprising:
    a strip of hook material attached at each distal free end for attachment to the loop material to facilitate a hook-and-loop connection.

15. A headgear to locate and retain a respiratory mask on a patient's head, comprising:
    a pair of upper side strap portions, each having proximal and distal free ends and a pair of lower side strap portions, each having proximal and distal free ends, wherein the upper side strap portions and the lower side strap portions each have a first section adjacent to their respective distal free ends and a second section adjacent to their respective proximal ends, said upper and lower side strap portions being wider in their second sections than in their first sections;
    a rear portion, having an upper rear strap portion, a lower rear strap portion, and an intermediate strap arrangement;
    the upper rear strap portion connecting the upper side strap portions at their proximal ends;
    the lower rear strap portion connecting the lower side strap portions at their proximal ends;
    the intermediate strap arrangement comprising:
       a pair of upper intermediate strap portions extending downward at an angle from each said proximal end of a respective one of the upper side strap portions, such that the upper rear strap portion and the pair of upper intermediate strap portions define a substantially-triangular upper opening; and
       a pair of lower intermediate strap portions extending upward at an angle from each said rear end of a respective one of the lower side strap portions, such that the lower rear strap portion and the pair of lower intermediate strap portions define a lower opening;
       wherein the upper intermediate strap portions and the lower intermediate strap portions connect at an intersection point located below the upper opening and above the lower opening.

16. The headgear as claimed in claim 15, wherein the angle between each upper side strap portion and the upper intermediate strap portion to which it is attached is greater than 90°.

17. The headgear as claimed in claim 16, wherein the angle between each lower side strap and the lower intermediate strap to which it is attached is greater than 90°.

18. The headgear as claimed in claim 15, wherein the upper rear strap portion has a curved portion of a predetermined radius, wherein the predetermined radius is measured when the headgear assembly is laid out flat; and
    wherein the curved portion extends between and connects to the upper intermediate straps of the intermediate strap arrangement, as well as the proximal ends of the upper side straps.

19. A respiratory mask assembly to deliver breathable gas to a patient, comprising:
    a full face mask having a mask frame;
    a headgear assembly as claimed in claim 18; and
    wherein an upper portion of said mask frame is attached to the headgear assembly by the upper side straps and a lower portion of said mask frame is coupled to the headgear assembly by the lower side straps.

20. The respiratory mask assembly according to claim 19, further comprising:
    a mask cushion permanently attached to the mask frame.

21. The respiratory mask assembly according to claim 19, further comprising:
    a clip to attach each said lower side strap to the mask frame, wherein each said lower side strap loops through an opening in each said clip.

22. The respiratory mask assembly according to claim 21, wherein each said upper side strap is attached to the upper portion of the mask frame by looping through an opening positioned at each side of the upper portion of the mask frame.

23. The headgear assembly as claimed in claim 15, further comprising:
    an outer layer of loop material to facilitate a hook-and-loop connection with a strip of hook material attached at the distal free end of each said upper side strap and each said lower side strap.

24. A respiratory mask assembly to deliver breathable gas to a patient, comprising:
- a mask frame and an adjustable forehead support;
- a headgear assembly as claimed in claim 15; and
- wherein said forehead support is attached to the headgear assembly by the upper side straps and said mask frame is coupled to the headgear assembly by the lower side straps.

25. The respiratory mask assembly as claimed in claim 24, further comprising:
- a mask cushion permanently or removably attached to the mask frame.

26. The respiratory mask assembly as claimed in claim 25, wherein the mask assembly is a nasal mask structured to deliver a breathable gas to a patient's nose.

27. The respiratory mask assembly as claimed in claim 26, further comprising:
- a detachable connector to attach each said lower side strap to the mask frame, wherein each said lower side strap loops through an opening in each said detachable connector.

28. The respiratory mask assembly as claimed in claim 27, wherein each said upper side strap is attached to the forehead support by looping through an opening positioned at each side of the forehead support.

29. A respiratory mask assembly to deliver a breathable gas to a patient, comprising:
- a mask frame and an adjustable forehead support;
- a headgear, the headgear comprising:
  - a pair of upper side straps and a pair of lower side straps;
  - two rear straps including an upper rear strap and a lower rear strap; and
  - an intermediate strap arrangement positioned between the two rear straps, wherein the intermediate strap arrangement includes a pair of upper intermediate straps angled relative to the upper rear strap and a pair of lower intermediate straps angled relative to the lower rear strap,
  - wherein the upper rear strap comprises a curved portion of a predetermined radius,
  - wherein the predetermined radius is measured when the headgear is laid out flat,
  - wherein the curved portion extends between and connects to the upper straps of the intermediate strap arrangement,
  - wherein the curved portion is structured to engage a posterior portion of the parietal bone of the patient's head in use,
  - wherein the pair of upper intermediate and lower intermediate straps converge towards and join at an intersection point,
  - wherein the pair of upper intermediate straps of the intermediate strap arrangement and the upper rear strap at least partially define a first opening,
  - wherein the lower rear strap and the pair of lower intermediate straps of the intermediate strap arrangement at least partially define a second opening; and
  - wherein only the upper side straps are adapted to connect the headgear assembly to the forehead support and only the lower side straps are adapted to connect the headgear to the mask frame.

30. A headgear to locate and retain a respiratory mask on a patient's head, comprising:
- an upper strap portion and a lower strap portion, each having a pair of distal free ends;
- an intermediate strap arrangement located between and connecting the upper and lower strap portion, the intermediate strap arrangement including a pair of upper intermediate strap portions attached at an angle to the upper strap portion, said pair of upper intermediate strap portions angled inwardly toward each other, wherein the intermediate strap arrangement defines two openings.

31. The headgear according to claim 30, wherein the upper and lower strap portions comprise an outer layer of loop material to facilitate a hook-and-loop connection.

32. The headgear according to claim 31, further comprising: a strip of hook material attached at each distal free end of each upper and lower strap portion to facilitate a hook-and-loop connection with the loop material of the upper and lower strap portions.

33. The headgear assembly according to claim 30, wherein the headgear assembly is symmetrical about a vertical axis located at the center of the headgear assembly and defined substantially perpendicularly to the pair of upper side straps and the pair of lower side straps, and wherein the two openings are symmetrical as the axis passes through the center of each said opening.

34. A headgear assembly to stabilize and position a respiratory mask assembly on a patient's head, comprising:
- a pair of upper side straps and a pair of lower side straps, each strap having a distal free end and a proximal end;
- a rear strap arrangement, comprising:
  - an upper rear strap to connect the pair of upper side straps at their respective proximal ends;
  - a pair of upper intermediate straps having upper and lower ends, each upper end connected to a respective upper side strap at its respective proximal end and the pair of upper intermediate straps converging towards one another at an angle from said respective proximal ends and being connected at their lower ends, said upper rear strap and said upper intermediate straps defining a substantially triangular-shaped opening; and
- wherein the upper rear strap comprises a curved portion of a predetermined radius structured to engage a posterior portion of the parietal bone of the patient's head in use, wherein the predetermined radius is measured when the headgear assembly is laid out flat, and wherein the curved portion extends between and connects to the upper ends of the upper intermediate straps;
- further wherein the upper side straps, the lower side straps, and the rear strap arrangement comprise a one-piece composite of soft material.

35. The headgear assembly according to claim 34, the rear strap arrangement further comprising:
- a pair of lower intermediate straps connected to respective proximal ends of the pair of lower side straps and respective lower ends of the upper intermediate straps.

36. The headgear assembly according to claim 34, wherein an outer layer of the one-piece composite material comprises a loop material.

37. The headgear assembly according to claim 36, further comprising:
- a strip of hook material attached at each said distal free end for attachment to the loop material, the hook material and the loop material defining a hook-and-loop connection.

38. A respiratory mask assembly to deliver breathable gas to a patient, comprising:
- a nasal mask having a mask frame and an adjustable forehead support;
- a headgear assembly as claimed in claim 34; and wherein said forehead support is attached to the headgear assembly by the upper side straps and said mask frame is coupled to the headgear assembly by the lower side straps.

39. The respiratory mask assembly according to claim 38, further comprising:
a mask cushion removably attached to the mask frame.

40. The respiratory mask assembly according to claim 38, further comprising:
a clip to attach each said lower side strap to the mask frame, wherein each said lower side strap loops through an opening in each said clip.

41. The respiratory mask assembly according to claim 40, wherein each said upper side strap is attached to the forehead support by looping through an opening positioned at each side of the forehead support.

42. A respiratory mask assembly to deliver breathable gas to a patient, comprising:
a full face mask having a mask frame;
a headgear assembly as claimed in claim 34; and
wherein an upper portion of said mask frame is attached to the headgear assembly by the upper side straps and a lower portion of said mask frame is coupled to the headgear assembly by the lower side straps.

43. The respiratory mask assembly according to claim 42, further comprising:
a mask cushion permanently attached to the mask frame.

44. The respiratory mask assembly according to claim 42, further comprising:
a clip to attach each said lower side strap to the mask frame, wherein each said lower side strap loops through an opening in each said clip.

45. The respiratory mask assembly according to claim 44, wherein each said upper side strap is attached to the upper portion of the mask frame by looping through an opening positioned at each side of the upper portion of the mask frame.

46. The headgear assembly according to claim 34, wherein the curved portion of the upper rear strap has a radius of curvature in the range of about 130.5 mm to about 187 mm.

47. The headgear assembly according to claim 46, wherein the curved portion of the upper rear strap has a radius of curvature of about 187 mm.

48. The headgear assembly according to claim 34, wherein the curved portion of the upper rear strap has a radius of curvature in the range of about 145 mm to about 170 mm.

49. The headgear assembly according to claim 48, wherein the curved portion of the upper rear strap has a radius of curvature of about 145 mm.

50. The headgear assembly according to claim 48, wherein the curved portion of the upper rear strap has a radius of curvature of about 166 mm.

51. The headgear assembly according to claim 48, wherein the curved portion of the upper rear strap has a radius of curvature of about 170 mm.

52. The headgear assembly according to claim 48, wherein the overall height of the headgear assembly is in the range of about 175 mm to about 215 mm.

53. The headgear assembly according to claim 52, wherein the overall height of the headgear assembly is about 175 mm.

54. The headgear assembly according to claim 52, wherein each lower side strap has a width in the range of about 17 mm to about 23 mm.

55. The headgear assembly according to claim 54, wherein each lower side strap has a width of about 20 mm.

56. The headgear assembly according to claim 54, wherein each lower side strap has a width of about 23 mm.

57. The headgear assembly according to claim 54, wherein each lower side strap has a width of about 17 mm.

58. The headgear assembly according to claim 54, wherein each upper side strap has a width in the range of 16 mm to about 22 mm.

59. The headgear assembly according to claim 58, wherein each upper side strap has a width of about 19 mm.

60. The headgear assembly according to claim 58, wherein each upper side strap has a width of about 16 mm.

61. The headgear assembly according to claim 58, wherein each upper side strap has a width of about 22 mm.

62. The headgear assembly according to claim 42, wherein the overall height of the headgear assembly is in the range of about 157.5 mm to about 236.5 mm.

* * * * *